United States Patent [19]
Norlander

[11] Patent Number: 5,536,369
[45] Date of Patent: Jul. 16, 1996

[54] FLUFF PULP AND METHOD FOR THE PREPARATION OF FLUFF PULP

[75] Inventor: Leif Norlander, Falun, Sweden

[73] Assignee: Stora Kopparbergs Bergslags Aktiebolag, Falun, Sweden

[21] Appl. No.: 256,022

[22] PCT Filed: Feb. 4, 1993

[86] PCT No.: PCT/SE93/00086

§ 371 Date: Aug. 30, 1994

§ 102(e) Date: Aug. 30, 1994

[87] PCT Pub. No.: WO93/16228

PCT Pub. Date: Aug. 19, 1993

[30] Foreign Application Priority Data

Feb. 14, 1992 [SE] Sweden ................. 9200460

[51] Int. Cl.⁶ .................. D21H 11/20; D21H 11/16
[52] U.S. Cl. .................. 162/157.6; 162/9; 162/182; 8/181; 8/195
[58] Field of Search .............. 162/9, 157.6, 158, 162/182, 164.6; 8/181, 195

[56] References Cited

U.S. PATENT DOCUMENTS

| | | | |
|---|---|---|---|
| 3,224,926 | 12/1965 | Bernardin | 162/146 |
| 3,993,640 | 11/1976 | Pickard et al. | 536/30 |
| 4,035,147 | 7/1977 | Sangenis et al. | 8/116.4 |
| 4,076,870 | 2/1978 | Yamamoto | 427/390 |
| 4,332,586 | 6/1982 | North | 8/186 |
| 4,770,668 | 9/1988 | Skoultchi et al. | 8/181 |
| 4,888,093 | 12/1989 | Dean et al. | 162/157.6 |
| 5,225,047 | 7/1993 | Graef et al. | 162/9 |

FOREIGN PATENT DOCUMENTS

WO88/04704  6/1988  WIPO.

Primary Examiner—Donald E. Czaja
Assistant Examiner—Jose A. Fortuna
Attorney, Agent, or Firm—Nixon & Vanderhye

[57] ABSTRACT

The invention relates to a fluff pulp for absorbent sanitary products consisting of cellulose with cross linkings between the cellulose molecules in the cellulose fibers, and a method for its preparation. The characteristics feature of the invention is that the chemical cross linkings between the cellulose molecules in the cellulose fibers are at least partly formed by a heterocyclic compound containing in addition to coal at least two nitrogen atoms in the ring. The specific volume of the pulp in wet state is at least 9 dm³/kg, its absorption capacity >11 g/g, and its brightness (dry sheet) is at least >65% ISO.

17 Claims, 5 Drawing Sheets

FLUFF PULP AND METHOD FOR THE PREPARATION OF FLUFF PULP

TECHNICAL FIELD

The present invention relates to fluff pulp for absorbent sanitary products, made up of cellulose with chemical cross linkings between the cellulose molecules in the cellulose fibres. The invention also relates to a method for preparing cellulose intended for use as fluff in absorbent sanitary products, which comprises cross linking of the cellulose fibres in the fluff pulp.

BACKGROUND TO THE INVENTION AND PRIOR ART

Consumers have, from their viewpoints, a number of demands concerning a good absorbent sanitary product, e.g. a napkin. The most important demands are that the napkin should be able to take up liquid and retain it during considerable time, also when subjected to compressive load. It is important that the wetting can be repeated, at which the napkin or the like on each wetting occasion can receive and distribute the liquid Within the napkin without leakage. Further, it should have an excellent absorption capacity. Furthermore, it should be soft and comfortable to wear, and must not contain any harmful or irritating agents. Moreover, the typical consumer appreciates that it has a high brightness. Yet, it must not be too expensive.

The demand specification above gives room for personal evaluations. Within the production branch there are yet a number of objective criteria for the quality determination of a fluff pulp. Thus the most important technical properties of a good fluff are:

—high absorption capacity and low time of absorption

—high specific volume wet

—high bulk after wetting, compression and spring back

—high rate of absorption

—high strength

—high brightness

Moreover the production requires that the pulp not contain or give off toxic, irritating or allergy-forming material, like e.g. formaldehyde, which is important not only for the consumer but also in the production.

In order to meet these requirements, various processes and ways to produce stiffer fibres to be used in fluff have been developed. The various ways are based on additives of various chemicals which work as a cross linking agent of the cellulose, i.e. to achieve chemical bonding between the cellulose molecules within the particular cellulose fibres, or the use of synthetic resins. Through the use of fibres, which are stiffer in wet condition, there is achieved a body of fluff giving increased absorption capacity and which moreover distributes the liquid throughout the whole volume of the fluff body. These properties of the fluff become of greater significance with the increased use of super absorbent polymers in products of type napkins and sanitary towels, which have resulted in a decreased total weight of the absorbent layer in these products.

U.S. Pat. No. 3,224,926 describes the use of formaldehyde for cross linking of cellulose in dry and defibrated state. However, formaldehyde as a cross linking agent is today questioned due to health aspects. The procedures described in the said patent moreover only have been examined in the laboratory and are not suited for implementation on a larger scale. Any commercial applications have not been realized based on this technology, as far as the applicant is aware.

EP-A-0 251 674, 0 251 676 and 0 252 650 describe the use of dialdehydes for dry chemical cross linking of defibrated fibres in the absence of fibre to fibre bondings. Dialdehydes, however, act in a similar way as formaldehyde, irritating to skin and mucous membranes. Even these reagents are therefor less suited in cellulose products which are to be used in close vicinity of the skin. As far as the applicant is aware of, nor have these processes been applied in a commercial scale.

EP-0 427 316 and 0 427 317 have recently proposed the use of polyvalent carboxylic acids, e.g. citric acid, for the cross linking of cellulose in fluff pulp at elevated temperatures. Some polyvalent carboxylic acids, however, have the disadvantage that they, at least during the preparation of the cellulose material, i.e. in the production line, are strongly irritating to the eyes. Some are moreover, at least at the present stage, very expensive and can therefor only be used for laboratory trials. These latter chemicals therefor have not achieved any commercial use as a cross linking agent for fluff pulp. Citric acid has been suggested as a cross linker and is commercially available, but the agent has an unfavourable influence on the final brightness of the cross linked fluff pulp.

Within the textile industry, the use of various cross linking chemicals to produce crease-proof cotton fabrics is well known, among them certain non-formaldehyde based reagents. Thus in June 1982, was proposed in Textile Research Journal, p. 357 ff, for said textile uses, additives of Glyoxal, polyacetal, bio-β-hydroxy ethyl sulfon, propylene glycol diglycidyl ether and glyoxal adducts of urea and its derivatives, among them dihydroxy ethylene urea (DHEU), dihydroxy dimethylene urea (DHHEEU) and dihydroxy methylethylene urea (DHDMEU). U.S. Pat. No. 4,770,668 has later proposed more complex derivatives of dihydroxy ethylene urea, still for the use as a crease-proof agent, i.e. as permanent press agents in cellulose based fabrics and fabrics made of cellulose/polymer mixtures.

In spite of large efforts in the US as well as in Europe and Japan within the area of development of absorbent sanitary products, no technically and commercially completely acceptable fluff pulp with chemical cross linkings between the cellulose molecules has been presented so far.

BRIEF DISCLOSURE OF INVENTION

The purpose of this invention is to offer a fluff pulp for absorbent sanitary products with excellent technical properties and without the problems mentioned above, which is possible with a fluff which is characterized by the following properties:

—that its specific volume in wet state >9 $dm^3$,

—that its absorption capacity > 11 g/g, and

—that the chemical cross linkings between the cellulose molecules in the cellulose fibres at least to some degree are made up from a heterocyclic compound containing in addition to carbon at least two nitrogen atoms in the ring.

The cross linked pulp according to the invention preferably has a brightness of at least 65% ISO, preferably at least 70% ISO, as measured on a dry sheet.

For the cross linking it is possible with advantage to employ certain of the above mentioned reagents which have been used in the textile industry to make fabrics based on cellulose, foremost cotton fabrics, crease-proof, namely dihydroxy ethylene urea, $C_3N_2O_3H_6$, or any derivative or derivatives thereof. Dihydroxy ethylene urea and many of its derivatives are thus commercially available at a low cost. They do not involve discomfort in the form of itching, irritation in the eyes or similar, neither for the producers nor for the users. At the same time, said regents give the desired technical effects in the fluff after curing. Among dihydroxy ethylene urea derivatives, those are useful in the fluff according to the invention, which on the one hand give the desired technical effects, on the other hand do not involve undesired effects, such as skin itching or irritation to the eyes, neither to the producers nor to the users. From the latter reason, one should avoid derivatives which may decompose into formaldehyde, a risk which exists along with derivatives containing functional groups consisting of e.g. $CH_2OH$.

Dihydroxy ethylene urea has the structural formula:

(1)

and its derivative may generally be described by the structural formula:

(2)

where R1 and R2 may be hydrogen or an alkyl group, $C_nH_{2n+1}$, where $n \geq 1$ or R1 is an alkyl alcohol group, $C_nH_{2n}OH$, where $n \geq 2$.

According to the present invention, various fibres may be used as raw material for the fluff pulp. In the examples which will be shown in the following, bleached sulphate pulp made from nordic softwood (mixture of spruce, *Picea abies,* and pine, *Pinus sulvestris*) has been used, but the invention may also be applied to other sulphate pullps or to sulphite pulps in bleached or unbleached condition, CTMP etc. As fibre raw materials, at least all softwood pulps with long fibres may serve, such as "south state pine" and nordic softwood, and also cellulose fibres of type esparto, hemp, flax etc. are conceivable.

The fluff pulp according to the invention can be prepared in different ways on an industrial scale. Acording to one of the methods of preparing the fluff, a cellulose pulp is produced in the form of a slurry/stock, which is formed to a web, which is pressed and dried. The cross linking chemical/s, according to the invention, is/are applied to the pulp at the latest before drying the web, which is carried out at temperatures below 100° C., at which temperatures the cross linking chemical/s is/are inactive. Said cross linking chemical/s is/are suitably added to the pulp after it has been dewatered to at least 20% dry solid content, preferably to between 30 and 50% dry solid content. The cross linking chemical is suitably added to the pulp of the press section in the wet machine, suitably in a glue press type of apparatus. The dried pulp is dry shredded—defibrated—at a temperature which also is below the curing temperature of the cross linking chemicals, i.e. preferably below 100° C. In order to release the cross linking mechanisms, the pulp is heat-treated at a reaction temperature of 130°–210° C., preferably at 150°–200° C., during a period of 0.5–30 min, preferably 1–10 min, at which the cross linking chemical/s is/are activated and cross linkings are produced between the cellulose fibres. Preferably, this activation is carried out on the dry shredded, i.e. defibrated pulp.

The defibration of the pulp may also be carried out in the wet state. According to an appropriate way to prepare the pulp on an industrial scale, according to the invention, the cross linking chemical/s can be added to the stock, which subsequently is dewatered. This can, by way of example, be carried out in a conventional wet press machine, which may comprise a cylinder-vat unit or a Fourdrinier wire, a press section and possibly a lead dryer (pre-dryer). Whichever equipment is chosen, the pulp is dewatered and a so called wet pulp is achieved with 40–60% dry solid content, preferably 40–50% dry solid content. Instead of adding the cross linking chemical/s to the stock, one may as an alternative add it/them to the pulp in the wet machine, suitably in the press section, e.g. in a glue press sort of apparatus. The wet pulp containing the cross linking chemical/s is defibrated in a disc refiner in one or several steps. The defibrated pulp is thereafter flash dried in a flash dryer prior to be heated up to the reaction temperature. Drying is suitably performed in several drying steps, of which the last can be used for heating the fibres to the appropriate temperature for the cross linking reaction to take place.

It is convenient to activate the cross linking chemical by feeding the dry shredded pulp, in dry or wet condition, continuously through a heating zone, through which the curing reaction can be controlled by regulating the temperature and the feed speed through the heating zone as well as the dwell time in the heating zone. It is preferable to use a tunnel oven as a heating zone, through which hot air is led, or if the risk of explosion must be reduced, a hot non oxidizing gas is led through said oven, suitably nitrogen, or a gas with a sufficiently low partial pressure of oxygen, so that the risk of explosion is eliminated. To feed the shredded pulp through the heating zone, one can use various continuously working conveyors, like worm conveyors, e.g. worm conveyors with perforated casings allowing for hot gas to flow through the fluff, as well as band conveyors. A convenient means of transport comprises two endless, wide-meshed wires, between which the shredded pulp can pass through the oven. However, it is quite possible to carry out the shredding batchwise in an oven.

By the present invention a fluff can be achieved with the following features, important for absorbent sanitary products:

Specific volume wet >9 $dm^3$/kg
Absorption capacity >11 g/g
Rate of absorption >0.6 ml/s at the fourth dosage
Brightness, dry sheet $\geq$70% ISO Further characteristics, aspects and advantages of the invention will be apparent from the appending claims and from the following description of performed experiments and the thereafter following description of a preferred embodiment of the method of the invention.

BRIEF DESCRIPTION OF DRAWINGS

In the following description of performed experiments and from a preferred embodiment of the method of the invention, reference will be made to the accompanying drawings, in which.

DESCRIPTION OF METHODS OF MEASUREMENT

Measuring specific volume and absorption properties according to Scan-C 33:80

Definitions

Specific volume: Volume of the test specimen in dry state (specific volume dry) or in wet state (specific volume wet) per mass unit (weight) of fluff.

Time of absorption: The time consumed to completely saturate a standardized test specimen of fluff with absorbed liquid (synthetic urine was used during trials) by testing under certain conditions.

Absorption capacity: Relationship between the mass (weight) of the liquid taken up by a standard test specimen of fluff under certain condition and the original mass (weight) of the test specimen.

Cylindrical test specimens of fluff with the mass 3 g and the diameter 50 mm were used at the measurements, which test specimens were formed in a particular test specimen former of the kind also described in Scan-C 33:80.

Figure 1:
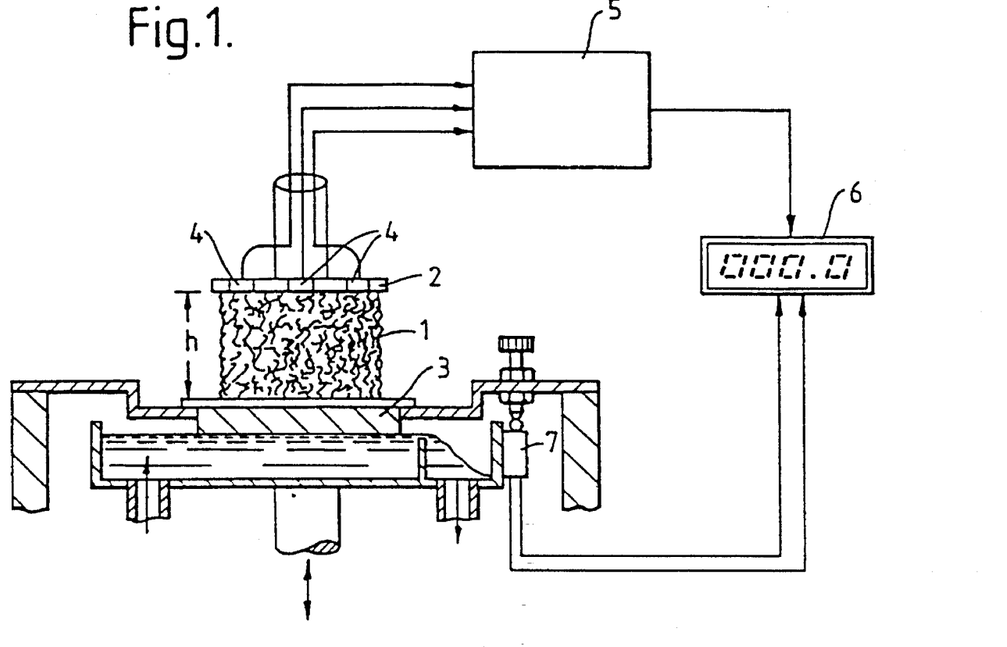
FIG. 1 illustrates how specific volume and fluff absorption properties are measured according to Scan-C 33:80.

An equipment of the type shown in FIG. 1 was used at the measurements. The test specimen 1 was placed vertically and a weight 2 of 500 g was placed on top of it. The height h of the test specimen is measured in dry and in wet condition, which gives necessary data to calculate the specific volume. The test specimen can absorb water from below through a perforated bed 3. The water level is adapted to allow the underside of the test specimen to only just dip into the water. The time recorder equipment (electrodes 4, logic unit 5, counter 6 and micro switch 7) starts in the same instance as the test specimen comes into contact with the water and stops when the water has found its way through the test specimen. The time of absorption is registered. The test specimen is allowed to absorb water for another 30 s, after which the water level is lowered. The test specimen is thereafter allowed to drain for 30 s, after which the weight 2 is taken away and the wet test specimen is weighed.

The specific volume is calculated from the expression X= A×h/10 w=0.655 h where

X= specific volume in $dm^3/kg$

A= the bottom area of the test specimen w= the mass of the dry test specimen in g (3.0 g)

h= the height of the test specimen under load in dry and in wet condition, respectively.

The absorption capacity is calculated from the expression Y= (b−w)/w, where

Y= the absorption capacity in g/g b= the mass of the wet test specimen in g

Measuring bulk and spring back in wet condition

The purpose of this method of measurement is to measure the spring back in wet condition after a compression. Test specimens are produced according to Scan-C 33:80, see above. Absorption meter is used according to Scan-C 33:80, see above. Further there is used a tube of transparent plastics with the height 98 mm, weights which give the loading of 0.7 kPa, 2.5 kPa and 7.5 kPa, a dosage pump and a measuring glass.

The measurements are performed using test specimens of 3 g. When performing the measurements, the test specimen is placed, without tube, in the absorption meter and a load of 0.7 kPa is put on top of it. After 30 s the height of the test specimen is read and noted as "original height at 0.7 kPa", which gives a proportion of "original bulk 0.7 kPa" expressed in $dm^3/kg$. The test specimen is thereafter loaded with 2.5 kPa. The height is read after 30 s and noted as "original height at 2.5 kPa", which gives "original bulk 2.5 kPa" in $dm^3/kg$. The test specimen is then placed in a tube and 20 ml water is metered evenly over the surface. The water is absorbed for 1 min, after which the test specimen is placed on a netting, still in the tube. The test specimen is loaded with 7.5 kPa and compressed for 7 min, whereafter the load is removed. The test specimen is then placed in the absorption meter and the tube is removed. The test specimen is loaded with 7.5 kPa and the height is read off after 30 s and noted as "bulk after wet compression at 7.5 Kpa", which will give "bulk after wet compression at 7.5 Kpa" expressed in $dm^3/kg$. The test specimen is then allowed to spring back for 7 min without tube, after which it is placed in the absorption meter without tube. The test specimen is now loaded with 0.7 Kpa and the height is read after 30 s and noted as "height after wet spring back at 0.7 Kpa", which gives a measurement of the "bulk after wet spring back at 0.7 kPa" expressed in $dm^3/kg$. Eventually, the test specimen is loaded with 2.5 kPa. The height is read after 30 s and noted as "height after wet spring back at 2.5 Kpa" which gives "bulk after wet spring back at 2.5 Kpa" in $dm^3/kg$. The bulk is calculated according to the formula:

$$Bulk\ (dm^3/kg) = height\ (cm) \times 0.6545 \times 10.$$

Measuring absorption rate (acquisition)

By these measurements the absorption rate was measured on a test specimen made in the laboratory. The test liquid, consisting of synthetic urine, was provided to the test specimen under load, after which the time consumed for the test specimen to absorb and receive the liquid was measured.

The test specimens were prepared by air-forming fluff. At the preparation of test specimens the pulp was subjected to a compressive pressure of 15 $kg/cm^2$ providing a solid integrated body with a sheet weight of 39 g and a diameter of 28 cm.

Figure 2:
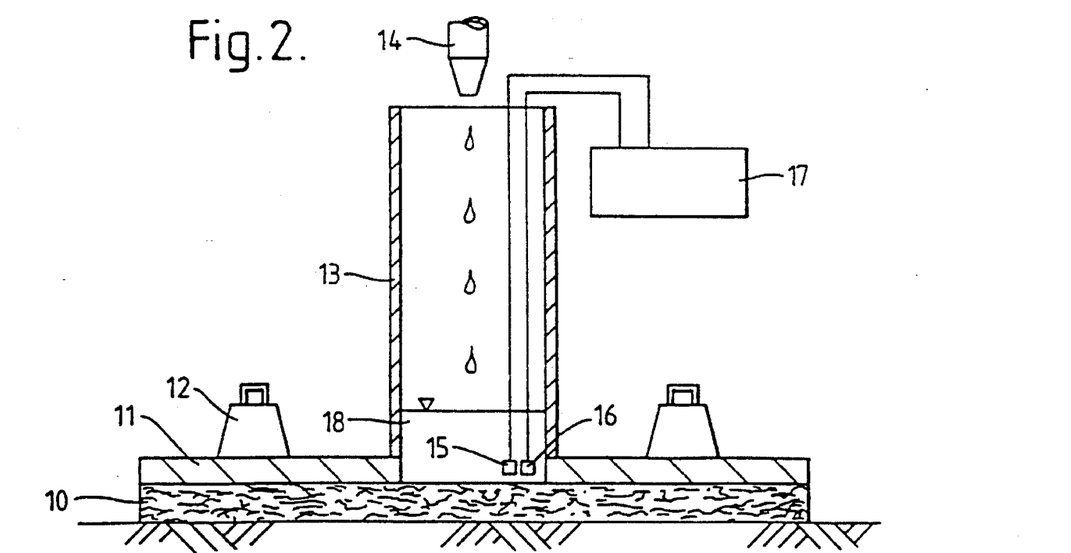
FIG. 2 illustrates a method for measuring rate of absorption in a napkin.

At the measurements there was used an equipment which is schematically shown in FIG. 2. The test specimen 10 prepared in the above described way, was placed under a plate 11, which in turn was loaded with weights 12 so that the test specimen 10 was subjected to a compressive pressure of 2.6 Kpa. In the rectangular plate 11 there is a circular hole, and to this hole there is connected a tube with the same diameter, 50 mm, as said hole. A dosing hose has been designated 14, a pair of electrodes in the bottom of the tube 13, just above the test specimen 10, have been designated 15, 16, and an electronic and time recording equipment have been designated 17.

The synthetic urine contained per liter: 9.0 g NaCl, 2.69 g $KH_2PO_4$, about 1.8 $Na_2HPO_4$, 0.1 g Rubin S, and the rest essentially destillated water. The liquid had a pH 6.1–6.4.

From the dosing hose 14, 50 ml of the liquid was dosed in 5 s down into the tube 13. The liquid in the tube has been designated 18. The time consumed for the test specimen 10 to absorb and distribute the liquid 18 was measured, i.e. the time consumed to empty the tube 13 from all of the liquid. Each measurement was carried out 4 times, i.e. 4 doses of synthetic urine were applied with 5 min intervals to the test specimen, each dose containing 50 ml of synthetic urine.

Measuring drip capacity

Figure 3:
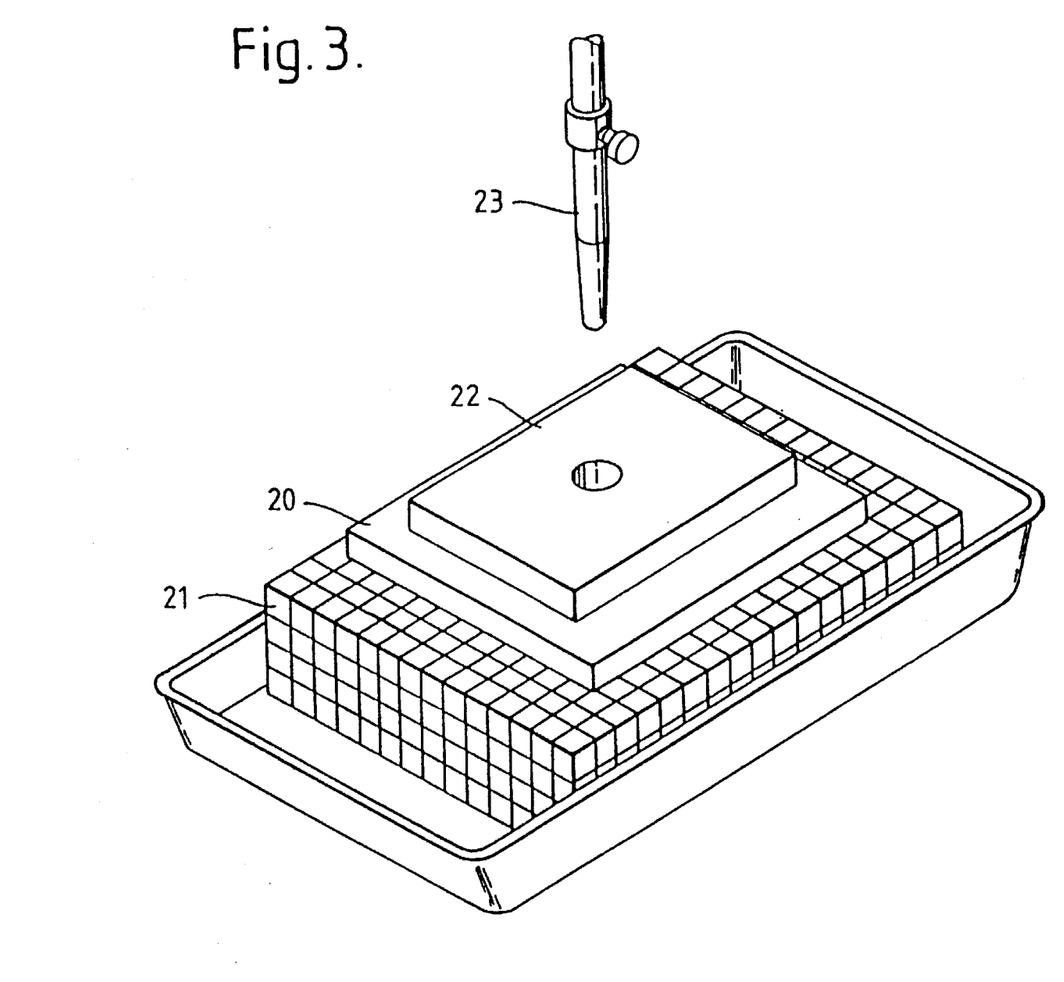
FIG. 3 illustrates how drip capacity in a fluff sample is measured.

This method of measurement has similarities with the recently described method of how to measure the absorption rate. Apart from the ability to receive and to transport the liquid away from the point where the liquid enters the test specimen, this measuring method also has the purpose to measure the fluff's ability to keep the liquid once received. The liquid as in the previous measurement consisted of synthetic urine, see above. An equipment of the type shown in FIG. 3 was used at the measurements. A circular test specimen 20 with the area 314 cm$^2$ and the mass 9 g was placed on a net 21 construction. The test specimen was charged with a load 22 exerting a compressive pressure of 0.5 kPa to the test specimen 20. The synthetic urine was applied to the centre of the test specimen 20 from a burette 23 at the rate 2 mils. The time consumed for the test specimen 20 to release the first drop of synthetic urine from underneath the test specimen was noted. The time in seconds is in this connection equivalent to the number of grams×2 of synthetic urine, and the drip capacity is the number of grams of synthetic urine per gram fluff (g/g).

EXPERIMENTS

In the following experiments, the pH was adjusted on all pulp impregnation solutions to 4.0–4.3 by the use of acetic acid.

The first series of tests—series of experiments I—had the purpose of measuring the specific volume in dry and wet state, the absorption properties, the bulk or compression and the spring back and diffusion time/rate under varying take up of cross linking chemicals. In all instances concerning fluff pulp according to the invention, dihydroxy ethylene urea (DHEU) is used as cross linking chemical in varying concentrations in aqueous solution in combination with a pair of different kinds of catalysts and in varying concentrations. All experiments were carried out on a laboratory scale.

Dry and weighed sheets of A4 size of bleached sulphate pulp of nordic softwood was immersed into the prepared chemical solution, i.e. in the solution consisting of DHEU+ catalysts in aqueous solution, and the liquid surplus was pressed out in a press between blotting paper. After drying on a cylinder dryer at 80° C., the sheets were weighed out, and the increase in weight was noted. The dried material was conditioned at 23° C. and 50% RH and was subsequently defibrated in dry state in a hammer mill of the type Kamas H01. The energy of defibration was noted. The defibrated material was placed in an oven at 160° C. for 6 min. The resulting product was used to prepare test specimens with the fibres dispersed in air for determination of the specific volume and absorption properties according to Scan-C 33:80, the spring back properties in wet condition and the diffusion rate according to the above described methods of measurement.

Six examples of fluff according to the invention, examples 1–6, were prepared and examined in this series of experiments I. A reference specimen was prepared from the untreated pulp in the same mill for defibration as the chemically treated test specimen, examples O-A.

Figure 4:
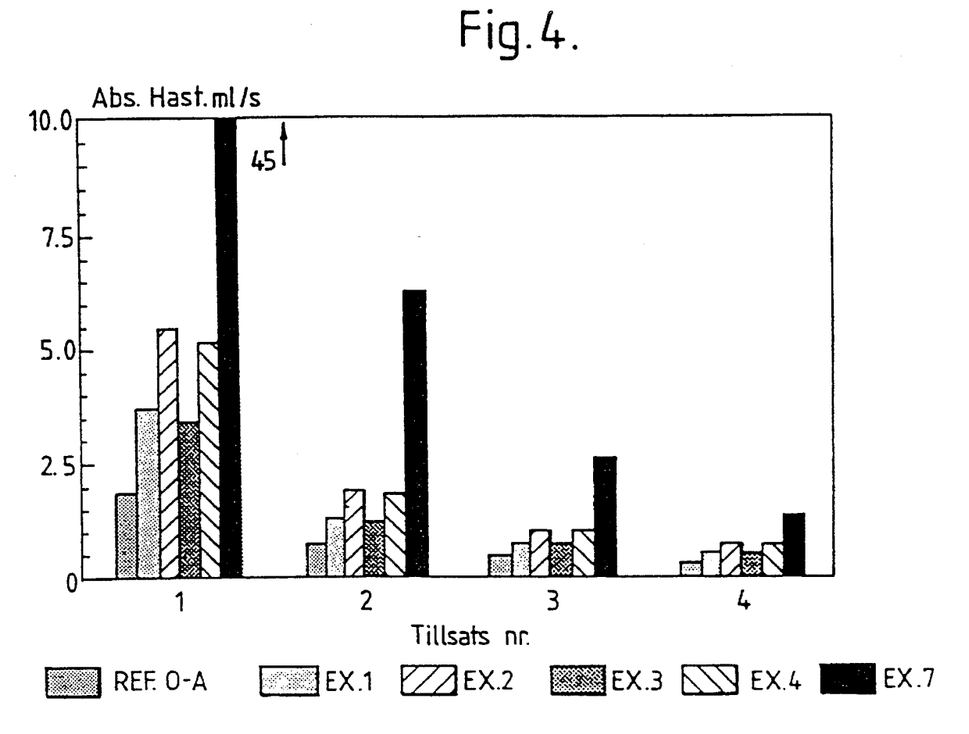
FIG. 4 shows by means of a bar chart how the absorption rate is dependent on the quantity and type of cross linking chemicals in a number of examined pulps.

The used solutions of chemicals, the amount of these solutions which was taken up by the pulp, curing temperature, curing time, and energy of defibration are given in table 1. The obtained results are summarized in table 2. The scattering of the test samples of examples 1–4 and 7 and of the reference material O-A is shown in FIG. 4.

From tables and diagrams can be concluded that the fluff according to the invention has superior properties, such as absorption rate and capacity, compared to conventional fluff, which does not contain any cross linking agents at all. Other properties which are desirable in absorbent products are influenced in a favourable way by the preparation according to the invention. Among the most important of these features is a high specific volume in wet state and a high spring back after load in wet state. Particularly good results are achieved in example 7, where the heat treatment was carried out at a somewhat higher temperature compared to the other examples and by means of hot air blowing through the bed. The example illustrates that benefits can be achieved through an optimization of the technical accomplishment of the process within the scope of the basic principles of the invention.

The test specimens in examples 5 and 6 and the reference material O-A were also analyzed as regards the content of formaldehyde extractable in water. It was noted that in all the test specimens the content was below the limit of detection, 1 ppm.

TABLE 1

Series of experiments I - Preparation of test specimens

| Solution of chemicals | Example | | | | | | | |
|---|---|---|---|---|---|---|---|---|
| | O-A | 1 | 2 | 3 | 4 | 5 | 6 | 7 |
| DHEU, g/l | — | 8.8 | 17.5 | 6.6 | 17.6 | 17.9 | 40.0 | 49.2 |
| MgCl$_2$, g/l | — | 4.9 | 10.0 | 1.6 | 4.1 | 4.1 | 16.9 | 5.5 |
| NaBF$_4$, g/l | — | 0.065 | 0.13 | — | — | — | 0.22 | — |
| Take up of solution of chemicals Take up, % | — | 2.2 | 4.4 | 2.3 | 5.9 | 5.8 | 9.2 | 4.8 |
| Curing temperature, °C. | — | 160 | 160 | 160 | 160 | 150 | 150 | 180* |
| Curing time, min | | 6 | 6 | 6 | 6 | 6 | 5 | |
| Energy of defibration kJ/kg | 215 | 207 | 199 | 222 | 217 | | | |

*The curing in Example 7 was carried out with hot air passing through a bed of fibres.

TABLE 2

Series of experiments I - Results
Specific volume and absorption properties, bulk after spring back wet and
diffusion time at varying take up of cross linking chemicals

| Example | Ref O-A | 1 | 2 | 3 | 4 | 5 | 6 | 7 |
|---|---|---|---|---|---|---|---|---|
| Specific volume dry, $dm^3/kg$ | 20.6 | 21.3 | 20.6 | 20.8 | 20.9 | 21.2 | 19.5 | 20.9 |
| Specific volume wet, $dm^3/kg$ | 8.2 | 9.4 | 9.5 | 9.1 | 9.6 | 9.5 | 8.9 | 10.5 |
| Time of absorption, s | 3.2 | 2.9 | 2.5 | 3.3 | 3.1 | 3.0 | 2.8 | 2.1 |
| Absorption capacity, g/g | 10.0 | 11.2 | 11.4 | 10.9 | 11.5 | 11.1 | 10.6 | 12.3 |
| Original bulk, 0.7 kPa $dm^3/kg$ | 31.5 | 32.3 | 32.6 | 32 | 32.8 | 33.4 | 32.1 | — |
| Original bulk, 2.5 kPa $dm^3/kg$ | 21.5 | 21.7 | 21.6 | 21.5 | 21.9 | 21.9 | 20.9 | — |
| Bulk after compression wet, 7.5 kPa $dm^3/kg$ | 6.1 | 6.5 | 6.8 | 6.5 | 6.6 | 6.5 | 6.5 | 7.2 |
| Bulk after spring back wet, 0.7 kPa $dm^3/kg$ | 7 | 7.5 | 8 | 7.6 | 8 | 7.8 | 7.2 | 8.9 |
| Bulk after spring back wet, 2.5 kPa $dm^3/kg$ | 6.5 | 7.1 | 7.4 | 7.1 | 7.3 | 8.0 | 7.4 | 8.3 |
| Absorption rate dose 1, 50 ml, ml/s | 1.9 | 3.7 | 5.5 | 3.4 | 5.2 | | | 45 |
| Absorption rate dose 2, 50 ml, ml/s | 0.7 | 1.3 | 2.0 | 1.2 | 1.9 | | | 6.3 |
| Absorption rate dose 3, 50 ml, ml/s | 0.5 | 0.8 | 1.1 | 0.7 | 1.0 | | | 2.6 |
| Absorption rate dose 4, 50 ml, ml/s | 0.3 | 0.5 | 0.8 | 0.5 | 0.7 | | | 1.4 |

In a series of experiments II, there were used test specimens prepared from bleached sulphate pulp. Chemical solutions were used with compositions according to table 3 below. As in the series of experiments I, the surplus liquid was pressed out in a press between blotting paper. After drying on a cylinder dryer at 80° C., the sheets were weighed out and the increase in weight was noted. The dried material was conditioned at 23° C. and 50% RH. In two of the experiments in this series of experiments II, examples 8 and 9, the dried material was then defibrated in dry state in a hammer mill, examples 8 and 9, after which the defibrated material was cured in an oven at 150° C. for 5 min. However, in one experiment, example 10, the defibration was carried out in dry state by means of a hammer mill after the material had been cured in an oven at 150° C. for 5 min. In all the three experiments, examples 8–10, the resulting products were used for preparation of test specimens with the fibres dispersed in air for determination of drip capacity and specific volume wet. As reference material, there were also in this case used test specimens prepared from the untreated pulp in the same mill as for the defibration of the chemically treated specimens.

The results are summarized in table 3. The drip capacity is further shown graphically in FIG. 5.

Figure 5:
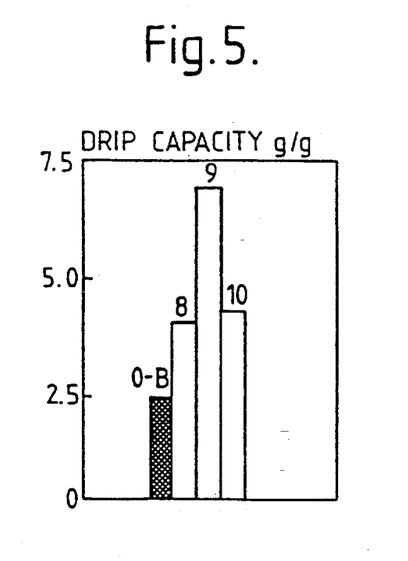
FIG. 5 is a bar chart showing the drip capacity of examined fluffs in a second series of experiments.

From table 3 and FIG. 5, one can conclude that the best result is achieved if the defibration is carried out prior to curing, i.e. before the cross linkings between the cellulose molecules are established.

From the results it can also be concluded that the take up of chemical solution in the pulp should be more than 1%, conveniently more than 3%.

TABLE 3

Series of experiments II
Composition of used chemicals

| Example | 8 | 9 | 10 |
|---|---|---|---|
| DHEU, g/l | 14.0 | 46.9 | 46.9 |
| $MgCl_2$, g/l | 5.8 | 19.5 | 19.5 |
| $NaBF_4$, g/l | 0.08 | 0.26 | 0.26 |

TABLE 4

Series of experiments II
Examination of specific volume and drip capacity at varying
take up of cross linking chemicals and significance of
defibration prior to curing or after.

| Example | Ref O-B | 8 | 9 | 10 |
|---|---|---|---|---|
| Take up of chemical solution Take up, % | 0 | 3 | 7.50 | 6.70 |
| Energy of defibration kJ/kg | 215 | 192 | 173 | 191 |
| Defibration prior to curing or after | | prior | prior | after |
| Drip capacity, 2 ml/s, g/g | 2.50 | 3.90 | 6.90 | 4.20 |
| Specific volume dry, $dm^3/kg$ | 21.10 | 20.50 | 20.40 | 19.20 |
| Specific volume wet, $dm^3/kg$ | 8.40 | 8.70 | 9.50 | 8.70 |

Series of experiments III

High brightness is a desirable property in absorbent sanitary products. In a series of experiments III, comparative examinations have been made concerning brightness of fluff according to the invention and of fluff that has recently been introduced on the market according to the preamble, at which citric acid has been used as cross linking agent. In all experiments, pulp with 44% dry solid content was dissolved in powder with water containing the cross linking chemicals. The pulp concentration in the pulper was about 3%. The dwell time in pulper and machine chest to roller press was kept at at least 15 min. The pulp suspension was dewatered in a roller press to a dry solid content of about 50%. None of the used chemicals is substantive to cellulose, why the proportion of chemical in pulp is determined in terms of how far the dewatering is driven. As a cross linking chemical there is used, according to the invention, 3,4-dihydroxy-2,5-dimethylethyleneurea (DHDMEU) in addition to a catalyst ($MgCl_2$), which was compared with citric acid (catalyst $Na_2HPO_4$). The different chemicals were added in amounts giving essentially equally results for DHDMEU and citric acid as regards specific volume wet and absorption capacity.

The brightness of the pulp prior to treatment was about 80° ISO as measured on dry sheet. The web from the roller press was shredded in a toothed screw to flakes with a size of about 1–3 cm. The flakes were defibrated by means of 20" disc refiner in two steps, rotation speed 3000 rpm, whereafter the defibrated pulp was dried in a flash dryer. The curing reaction was carried out batchwise under conditions specified in table 5.

TABLE 5

| Example | 11 | 12 | 13 | 14 | 15 | 16 | 17 |
|---|---|---|---|---|---|---|---|
| Cross linking agent | | Citric acid | | | | DHDMEU | |
| Curing time, min | 7 | 7 | 7 | 7 | 3 | 3 | 3 |
| Curing temperature, °C. | 180 | 180 | 180 | 180 | 170 | 170 | 170 |
| Brightness, dry sheet, % ISO | 61.5 | 59.1 | 60.2 | 54.8 | 73.6 | 73.9 | 75.1 |

From the results in table 5 it can be concluded that the brightness decreases in the pulp during cross linking; The brightness in the original material was approx. 80% ISO. While the brightness in pulp cross linked with citric acid is decreased with about between 18 and 25% ISO, the brightness in pulp cross linked with the DHEU-derivative DHDMEU, however, only decreases with some 5% ISO. To reach the same brightness in a pulp cross linked with citric acid as in a pulp according to the invention, one will have to bleach the original pulp to essentially over 80% ISO. Bleaching of pulp to such levels of brightness prior to cross linking with the purpose of reaching the desired final brightness requires increased input of bleaching chemicals, which is costly, and moreover increased use of bleaching chemicals may lead to increased environmental pollution with chlorinated organic substance. By the invention, such bleaching is not required in order to reach a brightness in the final product exceeding 65% ISO, preferably exceeding 70% ISO, wherefore the invention in this respect implies a great advantage from an environmental point of view.

The cross linking according to the invention can further be realized at a lower curing temperature and be performed quicker than citric acid. From a production economical point of view, this difference in curing temperature and curing time is not insignificant.

DESCRIPTION OF INDUSTRIAL PERFORMANCES

Figure 6:
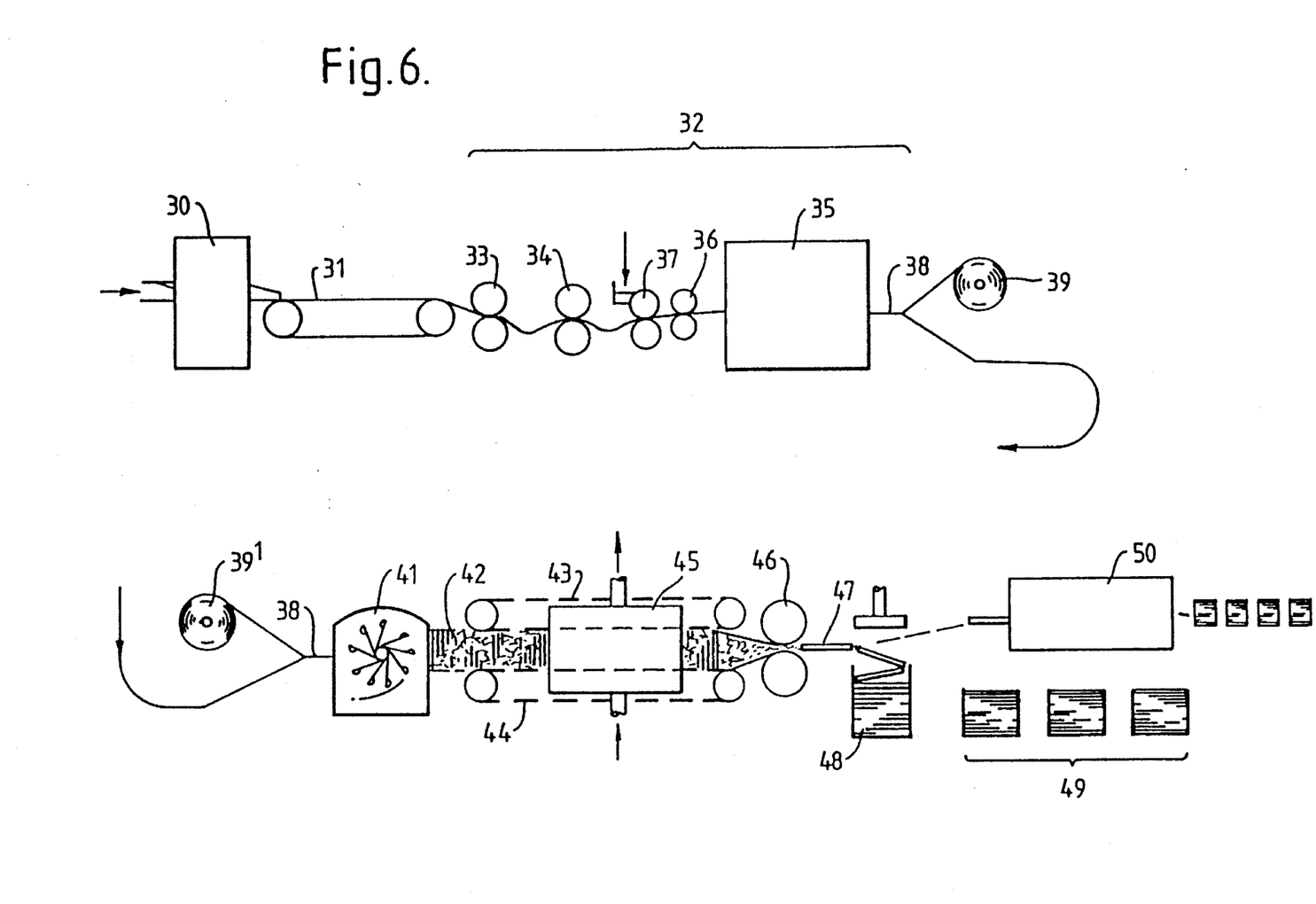
FIG. 6 is a flow chart which schematically illustrates a first preferred embodiment of the method for preparing fluff according to the invention.

FIG. 6 schematically illustrates a first method to implement the invention in full scale in continuously working processes. The upper part of the schematical flow chart in FIG. 6 shows how and where the cross linking chemicals can be added to the process, and the lower part of the schematical flow chart shows the further preparation, comprising defibration and curing.

From an inlet box 30 a stock is directed out on a wire section 31. A press section is generally designated 32. The press section comprises a number of presses 33, 34 and a dryer 35. The press section may also contain further presses in front of and after the dryer 35, which also may be denoted pre-dryer.

The cross linking chemicals used according to the present invention, i.e. dihydroxy ethylene urea (DHEU) and/or its derivatives in addition to catalyst/s are added to the web-formed cellulose sheet before drying according to the preferred embodiment, conveniently in the press section at a point where the pulp has a dry solid content reaching at least 20%, conveniently a dry solid content of 30–50%. Different methods and devices to apply the chemicals are possible to effectively incorporate them into the pulp material. By way of example, one can imagine spraying the chemical solution on the pulp from one or several transverse pipe/s provided with spraying nozzles, and subsequently render the chemicals integration more effective by means of a press 36. Preferably, however, the chemicals are conveniently added by means of an equipment 37 of the kind which is conventionally known as a glue press, which is a reliable technique to incorporate chemicals into comparatively thick and bulky sheets. The web material now containing the cross linking chemicals is dried in the dryer 35 at a temperature below the curing temperature of the chemicals, preferably at a temperature below 100° C.

Subsequent to the dryer 35, the web-formed sheet 38 may be reeled to reel bales 39 or—alternatively—be fed directly into a plant for defibration and curing. This unit is designated 40 in FIG. 6. The web material 38 is now directed into a defibrator 41. A convenient apparatus for dry defibration is the hammer mill, which occurs in various shapes. Other equipments to realize dry defibration are in principle useful as well, e.g. disc refiners, but a hammer mill is preferable when it comes to dry defibration.

Through the defibration in the apparatus 41, the material is fluffed and thus achieves large specific volume. At the same time it loses most of its fibre bonding properties and is consequently difficult to reform to a continuous web. It is however desirable to be able to carry out the curing, subsequent to defibration, under continuous conditions, allowing for regulation of curing time and temperature, and simultaneously assure that the pulp is treated uniformly in all parts of the bulky, fluffy material. According to a preferred performance, the fluffy pulp 42 is fed in between two endless, comparatively wide-meshed wires 43, 44. The shredded pulp is so to speak shut-in between the wires 43, 44 and is fed slowly through a tunnel oven 45. Hot gas flows through the oven 45. In principle said gas can be hot air, but it preferably consists of hot gas free from oxygen or gas with a very low partial pressure of oxygen in order to eliminate the risk of explosion. By regulating the feed speed of the wires 43, 44, the dwell time of the pulp 42 in the oven 45 is conveniently regulated to between 0.5 and 30 min, conveniently to 1–10 min. The temperature in the oven is regulated to between 130° and 210° C., conveniently to between 150° and 200° C., at which the cross linking chemicals are activated and perform the intended cross linkings between the cellulose molecules. After the treatment in the oven 45 the pulp is cooled, which can be carried out in a separate cooling zone.

The thus prepared material is subsequently again pressed in a press 46 to a more or less continuous material 47, which is folded and baled in a bale press 48. The finished bales are designated 49. Alternatively, the material 47 can be brought directly to a plant 50 for the manufacturing of napkins. This plant can in principle be connected directly after the oven 45, through which the need for repeated fluffing can be eliminated.

Figure 7:
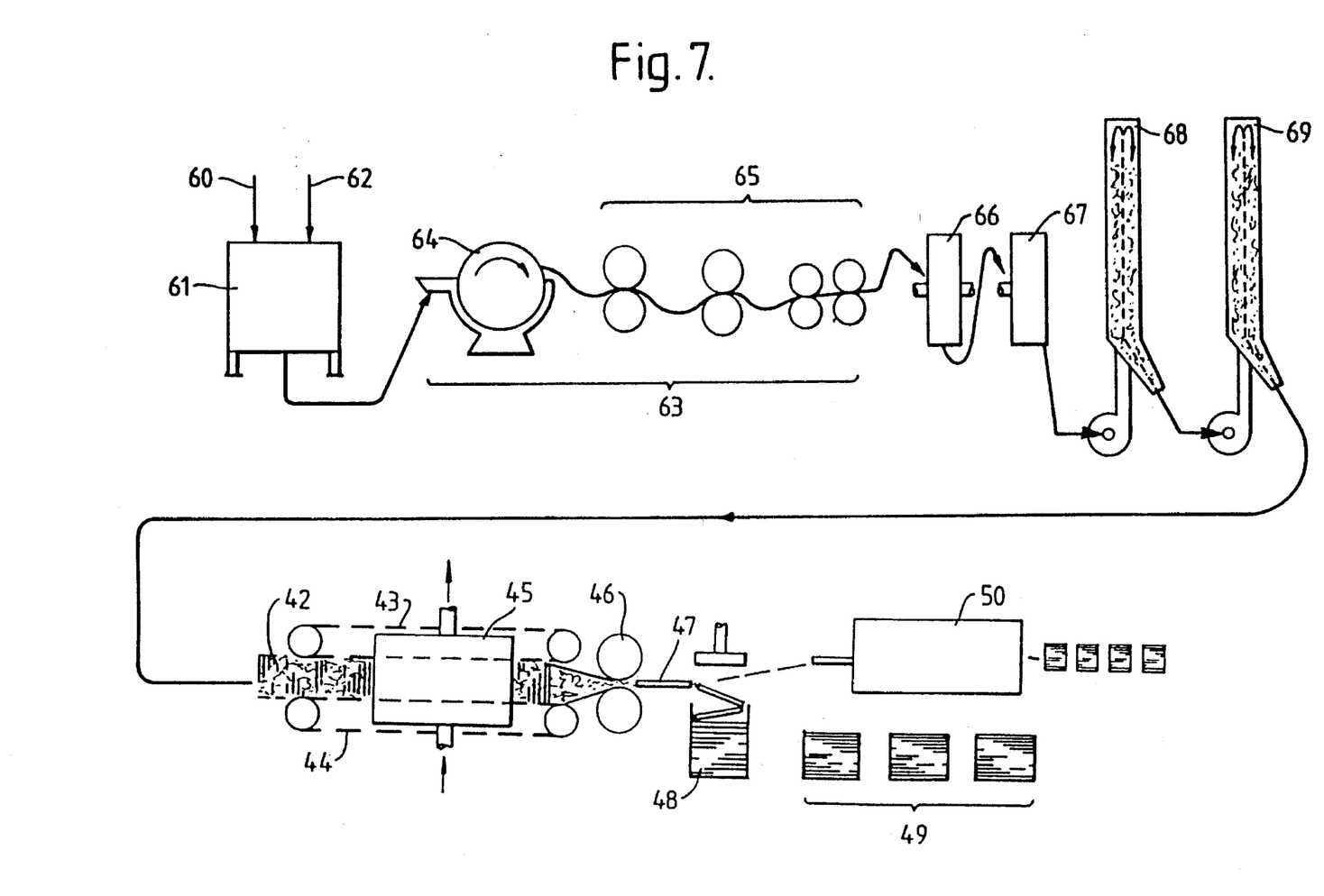
FIG. 7 is a flow chart which schematically illustrates a second preferred embodiment of the method of preparing fluff according to the invention.

FIG. 7 schematically shows an other way of implementing the invention on a full scale in continuously working processes. Reeled or baled pulp 60 is brought to a dissolver, or a pulper as it is called, 61, where the pulp 60 is slushed in water 62, which contains the cross linking chemicals. The thus obtained slurry is dewatered. This can take place in a wet press machine, generally designated denoted 63. In the example, the wet machine contains in a conventional way a cylinder-vat unit 64, and a press section 65. Possibly, there is a pre-dryer too. After dewatering, there is obtained a so called wet pulp, having a dry solid content of about 45–50%. The wet pulp is defibrated in disc refiners 66, 67 and subsequently dried in a flash dryer 68 at a temperature below 100° C. and eventually heated in another tower 69 to be homogenously and thoroughly heated just prior to the activation of the cross linking chemicals, which can be performed in the way described in connection with the previous example. This part of the process, concerning the units 42–50, therefor need not be further described here, but instead reference is made to the previous description.

I claim:

1. Method for preparing a cross-linked cellulose product suitable for use as fluff in absorbent sanitary products, said method comprising the steps of:

adding a cross-linking agent to a cellulose pulp material, said cross-linking agent being a heterocyclic compound having in addition to carbon at least two nitrogen atoms in the ring;

defibrating said pulp material containing said cross-linking agent in wet or dry state at a temperature below 100° C. to produce a defibrated pulp;

heating said defibrated pulp at a reaction temperature between 130° and 210° C. for 0.5–30 minutes, wherein said heterocyclic compound is activated and forms cross-links between the cellulose pulp; and forming a web or bale of said cross-linked cellulose pulp.

2. Method according to claim 1, wherein said cross-linking agent is dihydroxy ethylene urea, $C_3N_2O_3H_6$.

3. Method according to claim 1, wherein said cross-linking agent is a dihydroxy ethylene urea of the formula:

where R1 and R2 consist of groups which cannot decompose into formaldehyde.

4. Method according to claim 1, wherein in addition to said cross-linking agent there is also added to said cellulose pulp material at least one catalyst selected from the group consisting of salts of Mg, Ca, Na, Zn and Fe in the form of chlorides, nitrates, sulphates, carbonates and borates, alkali metal salts of fluoroborates $(BF)_4$ and organic amines.

5. Method according to claim 1, wherein said cross-linking agent is added to the pulp before it is dewatered, and the defibration is performed on dewatered wet pulp.

6. Method according to claim 1, wherein the amount of cross-linking agent is 0.1–10% by weight, based on the dry solid content of the pulp.

7. Method according to claim 1, wherein a catalyst is present in an amount of 0.1–10% by weight, based on the dry solid content of the pulp.

8. Method according to claim 1, wherein the brightness of the original pulp is lowered by not more than 10% ISO by the cross-linking treatment.

9. Method according to claim 1, wherein the defibrated pulp is heated continuously in a zone by passage therethrough of hot air or hot non-oxidizing gas or gas with sufficiently low partial pressure of oxygen.

10. Method according to claim 9, wherein the defibrated pulp is passed through said zone between a pair of endless wires.

11. Method according to claim 9, wherein the defibrated pulp is passed through a tunnel area between a pair of endless wires.

12. Method according to claim 1 wherein said cross-linking agent is a dihydroxy ethylene urea of the formula:

where R1 and R2 each represents hydrogen or an alkyl group of formula $C_nH_{2n+1}$, where $n \geq 1$ or R1 is an alkyl alcohol group of formula $C_nH_{2n}OH$, where $n \geq 2$.

13. Method according to claim 12, wherein said defibrated pulp is heated between 150° and 200° C. for 1–10 minutes.

14. Method according to claim 13, wherein said cross-linking agent is added to the pulp after it is dewatered to at least 20% dry solid content.

15. Method according to claim 14, wherein said cross-linking agent is added to the pulp after it is dewatered to 30–50% dry solid content.

16. Method according to claim 14, wherein said cross-linking agent is added to the pulp in a press section in a wet machine.

17. Method according to claim 16, wherein at least one cross-linking agent is added to the pulp in a glue press type apparatus.

* * * * *